United States Patent [19]

Imaizumi et al.

[11] 4,208,540
[45] Jun. 17, 1980

[54] PROCESS FOR SEPARATION AND RECOVERY OF ISOBUTENE

[75] Inventors: Masao Imaizumi, Tokyo; Mitsuo Yasuda, Hiroshima; Ko Sakata, Tokyo; Noboru Hirano, Yokohama, all of Japan

[73] Assignee: Nippon Oil Co., Ltd., Tokyo, Japan

[21] Appl. No.: 43,186

[22] Filed: May 29, 1979

[30] Foreign Application Priority Data

Dec. 22, 1978 [JP] Japan .............................. 53/160792
Feb. 14, 1979 [JP] Japan .............................. 54/15859

[51] Int. Cl.² .............................................. C07C 7/01
[52] U.S. Cl. .................................................. 585/809
[58] Field of Search ............................... 585/809, 856

[56] References Cited

U.S. PATENT DOCUMENTS

| | | | |
|---|---|---|---|
| 3,527,829 | 9/1970 | Horie et al. | 585/809 |
| 3,646,237 | 2/1972 | Horie et al. | 585/809 |
| 3,651,165 | 3/1972 | Horie et al. | 585/809 |
| 3,989,762 | 11/1976 | Ester | 585/809 |
| 4,012,456 | 3/1977 | Chaplits | 585/856 |

FOREIGN PATENT DOCUMENTS

| | | | |
|---|---|---|---|
| 150109 | 9/1962 | U.S.S.R. | 585/809 |
| 191507 | 2/1969 | U.S.S.R. | 585/809 |

*Primary Examiner*—George Crasanakis
*Attorney, Agent, or Firm*—Jordan and Hamburg

[57] ABSTRACT

A process for the continuous separation and recovery of isobutene from an isobutene-containing hydrocarbon mixture, comprising the steps of contacting the mixture with water to obtain a tertiary butanol-containing mixture, separating this mixture into hydrocarbon and aqueous layer, distilling the hydrocarbon layer to obtain a tertiary butanol-rich stream, dehydrating the thus obtained stream to obtain an isobutene-containing gaseous mixture and then introducing the thus obtained mixture into a distillation means to recover isobutene as the product therefrom.

14 Claims, 3 Drawing Figures

PROCESS FOR SEPARATION AND RECOVERY OF ISOBUTENE

This invention relates to a process for the effective separation and recovery of isobutene from a C₄ hydrocarbon mixture using an ion exchange resin as a catalyst.

There have heretofore been industrially carried out processes for separating isobutene, such as the Standard process (U.S.Pat. No. 2,388,971, Japanese Patent Gazettes Nos. 6165/66 and 7684/66) and Badger-CFR process (Hydrocarbon Processing Vol. 42, No. 11, p. 186 (1963)), however, these conventional processes have raised many problems as to countermeasures against corrosion by sulphuric acid, disposal of waste sulphuric acid, and the like. To overcome these difficulties, there have been proposed isobutene separation processes using no sulphuric acid as illustrated below.

Japanese Patent Gazette No. 41882/72 discloses a process for the recovery of isobutene comprising the steps of selectively reacting the isobutene contained in a C₄ hydrocarbon mixture with methanol in the presence of a cation exchange resin as the catalyst to separate the isobutene in the form of methyl tertiary-butyl ether from the C₄ mixture and then effecting the vapor phase decomposition of the thus separated methyl tert.-butyl ether in the presence of a metal-carried solid catalyst at higher than 250° C. to recovery the isobutene therefrom, however, this propsoed process raises problems as to difficulties in the construction of an apparatus to be used, caused by the use of high temperatures in the endothermic reaction in the process and also as to a loss of the methanol which is otherwise to be recycled for re-use.

In addition, U.S. Pat. No. 4,012,456 (of Japanese Patent Application Laying-Open Gazette No. 59802/76) discloses as isobutene recovery process comprising the steps of selectively reacting the isobutene contained in a C₄ hydrocarbon mixture with water in the presence of a cation exchange resin as the catalyst to separate the isobutene in the form of tertiary butanol from the C₄ mixture and then dehydrating the thus separated tertiary butanol to recover the isobutene therefrom, however, this known process has the disadvantages that it needs a large amount of the cation exchange resin as the catalyst due to the dehydrating reaction of tertiary butanol in vapor phase thereby resulting in the enlargement of an apparatus to be used and that it raises problems as to technical difficulties caused by the external supply of heat necessary for the dehydration reaction, the problems being such that remarkable difficulties will inevitably be encountered in the manufacture of an apparatus to be used since the catalyst has low heat resistance thereby rendering the use of a high-temperature heat source impossible and the heat necessary for the endothermic reaction is supplied from a comparatively low-temperature heat source thereby necessitating a very large heating surface.

As a result of their study in attempts to find an isobutene separation process having none of the aforesaid conventional disadvantages, the present inventors have found such a process for the continuous separation and recovery is isobutene which comprises the steps of:

(1) contacting an isobutene-containing hydrocarbon mixture with water at a temperature of 50°-150° C. in the presence of a cation exchange resin as the catalyst to obtain a reaction mixture containing tertiary butanol (hereinafter referred to as "TBA"), (2) separating the thus obtained TBA-containing mixture into a hydrocarbon layer and an aqueous layer, (3) distilling the hydrocarbon layer to recover the unreacted hydrocarbons as the top and obtain a TBA-rich stream as the bottoms, (4) distilling the aqueous layer from the step (2) to obtain the following three streams:
 (i) a stream (lighter fraction) containing the unreacted hydrocarbons previously contained in said aqueous layer,
 (ii) A TBA-rich stream (light fraction) and
 (iii) a stream of the water-rich fraction (less light fraction), (5) introducing the TBA-rich stream from the step (3) and the TBA-rich stream (ii) from the step (4) continuously into a dehydration reactor containing a cation exchange resin catalyst and a liquid mixture of 20-70 wt.% of TBA with water at a temperature of 90°-180° C. and a pressure of 1.5-15 Kg/cm²G, to effect the dehydration of the TBA, the TBA-rich stream from the step (3) being, if desired, further distilled to remove the remaining hydrocarbons therefrom just before being introduced into said dehydration reactor, (6) withdrawing a mixture of produced gaseous isobutene, gaseous unreacted TBA and steam continuously from the dehydration reactor at the top, (7) introducing the thus withdrawn gaseous mixture into a distillation tower to recover isobutene as the product therefrom at the top while recycling the whole or a part of the remaining fraction to said dehydration reactor, (8) withdrawing continuously from said dehydration reactor a part of the liquid mixture of the unreacted TBA and water contained therein and (9) subjecting the thus withdrawn liquid mixture to distillation in a distillation tower to withdraw a liquid stream containing the greater part of the water from the tower at the bottom and recover a mixture containing TBA in a high concentration and water therefrom at the top, the mixture so recovered being recycled to said dehydration reactor.

The process of this invention will be explained hereinbelow by reference to the accompanying drawing in which.

Figure 1:
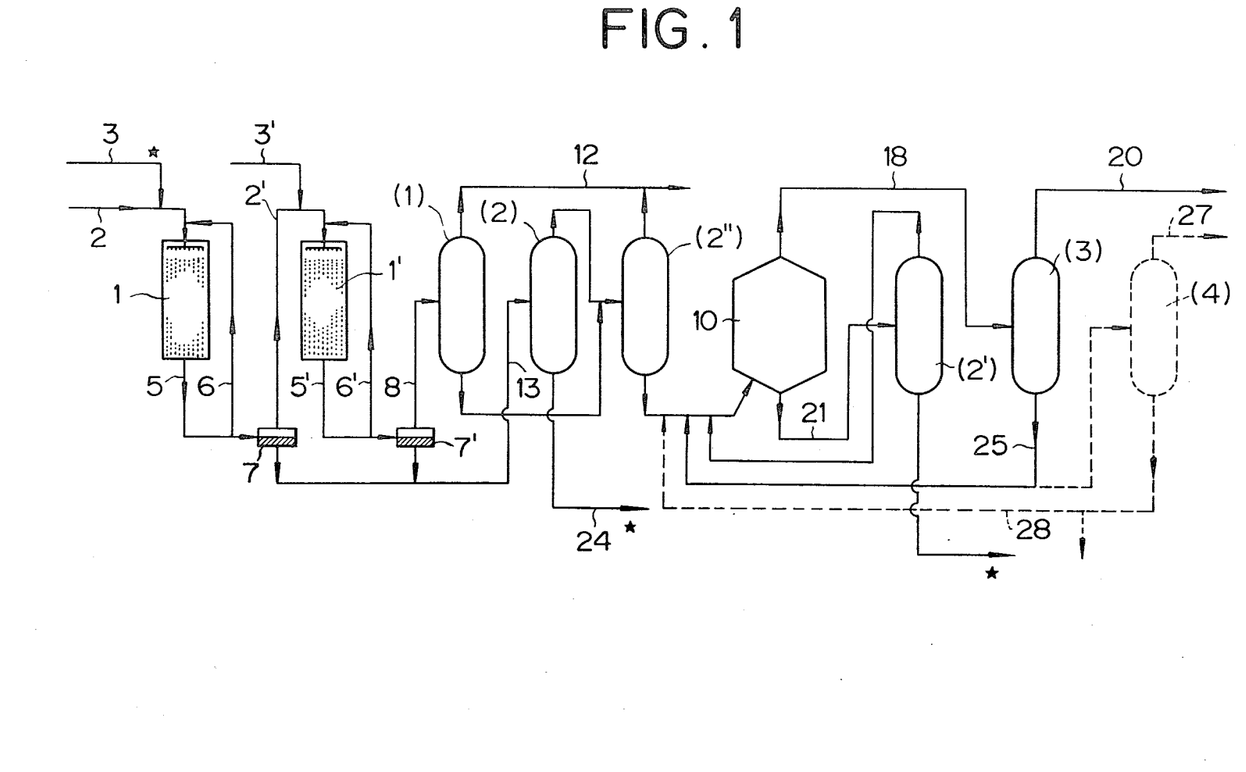
FIGS. 1-3 are each a flow diagram illustrating the practice of this invention.

Referring now to FIG. 1, an isobutene-containing hydrocarbon mixture liquefied under pressure is fed continuously into a first reactor (hydration reactor) 1 through a line 2. The isobutene-containing hydrocarbon mixture is generally a mixture of butenes, butane and the like, the mixture containing at least 10% of isobutene. There may industrially be used a C₄ hydrocarbon mixture obtained by the thermal, steam, catalytic or like cracking of petroleum. Such a C₄ hydrocarbon mixture from which the butadiene has been separated for removal may preferably be used. The content or concentration of isobutene in the hydrocarbon mixture is usually less than 80%, generally in the range of 20 to 50%. The isobutene-containing hydrocarbon mixtures used herein are hereinafter referred to as a "C₄ mixture" for brevity.

In the first reactor the continuously incoming isobutene is hydrated with water continuously fed into the first reactor through a line 3 to produce TBA in the presence of a strongly acidic cation exchange resin preferably as the fixed bed catalyst.

The strongly acidic cation exchange resins used herein are made basically of a styrene-divinylbenzene copolymer as the skeleton of the resin, and the particularly important factors on which their performances or properties depend are their exchange capacity, particle size, specific gravity, degree of crosslinking, surface area, porosity and the like. Among these strongly acidic cation exchange resins, those having a surface area, porosity, exchange capacity and particle size each in a specific range are preferred.

As for the surface area, the exchange resins used herein should preferably have a surface area of 0.2–120 $m^2/g$, preferably 0.4–100 $m^2/g$, when they are dried in vacuo at 80° C. for 6 hours and measured for surface area using nitrogen in accordance with the planimetric method of BET. When acidic cation exchange resins having a surface area of less than 0.2 $m^2/g$ are used, the hydrating reaction velocity will be low; on the other hand, the use of such resins having a surface area of more than 120 $m^2/g$ will raise problems as to their durability and mechanical strength. As for the exchange capacity, the exchange resins used herein should have a porosity of preferably at least 0.03 ml/ml, more preferably 0.05–1.0 ml/ml, as determined using mercury in accordance with the process described in "Prac. Natl. Acad. Sci., Vol. 7, 115 (1921)". The low porosity will result in the disadvantageous decrease of the hydrating reaction velocity. Resins which are usually called "gel type resins" have a porosity outside the aforesaid range, and resins of the type having a predetermined porosity in their structure may preferably be used in the practice of this invention.

As for the exchange capacity, the exchange resins used herein should preferably have an exchange capacity of at least 1.0 meq/g, preferably 2.0–6 meq/g, a particle size of 0.1–5 mm and a true specific gravity of 1.0–1.4. The exchange capacity is expressed by meq (milligram equivalent) of sulfonate group per gram of dried catalyst particles, and the use of an exchange resin having an exchange capacity of less than 1.0 meq/g will result in the decrease of the hydrating reaction velocity.

It is unsuitable to use exchange resins having a particle size of finer than 0.1 mm as a fixed bed to be filled, and those having a particle size of larger than 5 mm have decreased activity. It is desirable that the exchange resins used herein also have a divinylbenzene content (degree of crosslinking) of 1–15%.

The strongly acidic cation exchange resins having the aforesaid various specific properties may be prepared by suspension copolymerizing different monomers (such as styrene and divinylbenzene) in a solvent (such as tertiary amyl alcohol, secondary butyl alcohol or isooctane) which is good but little capable of swelling the resulting copolymer to produce a high molecular weight compound, and then sulfonating the thus produced compound.

As mentioned before, in this invention, the isobutene-containing hydrocarbon mixture is hydrated with water by contacting them with each other at 50°–150° C., preferably 60°–100° C., in the presence of the cation exchange resin to obtain a reaction mixture containing TBA.

It is preferable that this hydration reaction be carried out in a liquid phase. The thus obtained reaction mixture contains the unreacted hydrocarbons, TBA, water and, as the by-products, isobutene dimer etc. the contact conditions under which the hydrating reaction is effected are not particularly limited, however, it is very preferable that the following contact means be employed.

The first reactor 1 is usually cylindrical and lengthwise in shape and is filled with a particulate catalyst on a wire net or perforated plate placed on the bottom of the reactor. In the reactor, the space other than that substantially occupied by the catalyst is filled with the isobutene-containing $C_4$ hydrocarbon mixture in a continuous phase and, on the other hand, the water to be reacted with the hydrocarbon mixture is continuously introduced into the reactor through a scatterer provided at the top thereof and flows down the surfaces of the catalyst particles. The reason why the water can flow down as mentioned above is that it is gravitated down and has a higher specific gravity than the isobutene-containing hydrocarbon mixture in the continuous phase.

The isobutene from the hydrocarbon mixture is dissolved in the filmy streams of water with which the catalyst particles are covered, and the isobutene is catalytically reacted (hydrated) with the water on the surfaces of the catalyst particles.

In a case where the water and isobutene are contacted with each other in the aforesaid manner, the hydration of isobutene will proceed efficiently to produce TBA in a high yield with substantially no attendant formation of by-products such as isobutene polymers even if the aqueous and hydrocarbon phases are not homogeneous nor uniform.

The reason why such an excellent dehydrating reaction may be effected is not clear, however, it is considered as being due to the specific manner of contact between water and isobutene on the surfaces of catalyst particles, the compatibility of isobutene and water with the catalyst surface, and adsorption of isobutene and water thereon, and the like.

In FIG. 1, it was already indicated that the $C_4$ hydrocarbon mixture in the continuous phase flows continuously from the top of the reactor towards the bottom thereof, however, it is also possible that the $C_4$ hydrocarbon mixture is introduced into the reactor at the bottom, then transferred upward in the continuous phase as a whole and withdrawn from the reactor at the top although this alternative procedure is not shown in the Figure.

The aforesaid contact procedure according to this invention may be started effectively as illustrated below.

Prior to starting the operation according to this invention, a liquid hydrocarbon mixture (as isobutene-containing hydrocarbon mixture or an inert hydrocarbon mixture, for example) is filled in the reactor. Then, according to this invention, the $C_4$ hydrocarbon mixture and water start to be introduced into the reactor through lines 2 and 3, respectively, after which the reactants so introduced are gradually raised in temperature for starting the hydrating reaction. The $C_4$ mixture and water are introduced respectively through lines 2 and 3 as mentioned before; at the initial stage of the operation, however, there may be employed a means for filling up the reactor with the $C_4$ mixture by withdrawing the water in a more amount and then raising the contents of the reactor in temperature.

The hydrating reaction is effected at a temperature of 50°–150° C., preferably 60°–100° C. The use of a temperature lower than 50° C. will decrease the hydrating reaction velcoity thereby not to produce TBA effectively, while the use of a temperature higher than 150° C. will not only increase the amount of by-products such as isobutene dimer, isobutene trimer and secondary butyl alcohol but also degrade the catalyst badly.

The pressures used herein are not particularly limited; however, they should be such that the isobutene-containing hydrocarbon mixture and water are kept liquid at said reaction temperatures, and they may be usually 2–50 Kg/cm$^2$G, preferably 5–40 Kg/cm$^2$G.

It is preferable that the strongly acidic cation exchange resins be wetted thoroughly with water prior to their use. This is achieved by immersing the strongly acidic cation exchange resin in quantities of water at 0°–100° C. for about 1 minute to 24 hours. The use of the exchange resins so previously wetted in this manner will inhibit the production of by-products, particularly isobutene polymers, and prevent the degradation of catalytic activities to a great extent.

In this case, it is recommendable that the exchange resin in the dry state is filled in the reactor, water is introduced into the resin-filled reactor to contact the resin therewith, the remaining water is withdrawn from the reactor and then the reactor is filled up with the isobutene-containing hydrocarbon mixture in the same manner as above.

The water to be used is supplied to the reactor at an average linear velocity of at least 1.0 m/hr, preferably 1.0–30 m/hr and more preferably 1.5–20 m/hr, on the empty tower basis (or superficial velocity in the tower). The use of an average linear velocity of less than 1.0 m/hr will decrease the ratio of conversion of isobutene to TBA while it tends to promote the polymerization of butenes. On the other hand, the use of an average linear velocity of more than 30 m/hr will likewise decrease the ratio of conversion of isobutene to TBA and also decrease the concentration of TBA in the aqueous solution thereby tending to cause inconveniences in the subsequent operation. The C$_4$ mixture is passed at an average linear velocity of 0.2–50 m/hr, preferably 1–30 m/hr, on the empty tower basis in the reactor.

Water and the C$_4$ mixture are each supplied at a LHSV of 0.1–5.0 hr$^{-1}$, preferably 0.2–4 hr$^{-1}$, more preferably 0.3–1.5 hr$^{-1}$, with respect to the catalyst.

The reaction mixture obtained by the catalytic reaction as previously mentioned is withdrawn through a line 5 into a separation receptacle or separator 7 where it is separated into an aqueous layer and a hydrocarbon layer, the TBA being distributed in both the layers. The effluent (reaction mixture) through the line 5 may be partly recycled to the reactor through a line 6 thereby to control the temperature in the reactor and effect a uniform reaction, thus achieving an effective reaction. In this case, it is preferable that the effluent by recycled at a LHSV of 0.1–30 hr$^{-1}$, preferably 0.2–10 hr$^{-1}$, thereby obtaining a satisfactory result. An insufficient amount of the effluent recycled will not be effective in controlling the temperature in the reactor, while an excessive amount thereof recycled will decrease the ratio of conversion of isobutene to TBA.

According to this invention, the hydrating reaction may be effected in plural steps. Such a multistep reaction operation is illustrated in FIG. 1 which indicates two reactors for hydration. Referring to the Figure, the reaction mixture withdrawn through the line 5 is introduced into the separation receptacle 7 where it is separated into a hydrocarbon layer and an aqueous layer, the former layer being then introduced through a line 2' into a first reactor 1' which is the same as the first reactor 1. In this case, it is effective in increasing the ratio of recovery of isobutene from the C$_4$ mixture to install a device (not shown) for separating from the hydrocarbon layer the TBA contained therein between the line 2' and the first reactor 1'. In this case, it is preferable to supply the thus separated TBA to the subsequent or following distillation tower (1) or (2). Further, in a case where the hydrating reaction is carried out by the use of multiple hydration reactors, it is preferable in obtaining isobutene in a high yield that the reaction temperature used in each of the second and subsequent reactors be equal to, or 1°–20° C. lower than, that used in the first hydration reactor. The reaction mixture withdrawn from the last hydration reactor is passed to a separation receptacle 7' where it is separated into an aqueous layer and a hydrocarbon layer, after which the hydrocarbon layer is supplied through a line 8 to the distillation tower (1). Then, a TBA-rich stream is withdrawn from the distillation tower (1) at the bottom, while an unreacted C$_4$ hydrocarbon mixture from which the greater part of the isobutene has been removed through a line 12 is obtained from the tower (1) at the top. The C$_4$ mixture so obtained may be effectively used as material for organic synthesis. The TBA-rich stream usually contains 50–95 wt.% of TBA, 0.01–3.0 wt.% of the unreacted hydrocarbons and 5–50 wt.% of water. The TBA-rich stream is supplied, without heating or after heating, to a second reactor (dehydration reactor) 10, however, it is preferable that this stream be introduced into a distillation tower (stripping tower) (2″) prior to being supplied to the second reactor 10, to remove the unreacted hydrocarbons from the stream. In addition, the TBA-rich stream does not have to be wholly supplied to the stripping tower and may be partly used as starting materials in the other industrial fields, however, it is preferable that the greater part of the TBA-rich stream be supplied to the stripping tower for the subsequent dehydrating decomposition. The TBA-rich stream from the bottom of the stripping tower may be subjected to dehydrating decomposition without or with previous heating.

On the other hand, a part or the whole of the aqueous layer obtained by subjecting the hydration reaction products (reaction mixture) to phase or layer separation in the separation receptacle 7 or 7' is likewise supplied to the second reactor 10. Prior to being introduced into the reactor 10, the aqueous stream from the receptacle 7 or 7' is supplied to the dillation tower (2) to obtain a water-rich stream at the bottom thereof and a mixture of water with TBA (preferably 50–88 wt.%) at the top or upper portion thereof, the mixture being further distilled to remove the remaining unreacted hydrocarbons therefrom through the top of the tower.

At any rate, the aqueous layer from the receptacle 7 is distilled to be separated into the following three streams or fractions (i) to (iii):
  (i) a stream (lighter fraction) containing the unreacted hydrocarbons remaining and dissolved in the aqueous layer,
  (ii) a TBA-rich stream (light fraction) and
  (iii) a water-rich (aqueous) stream.

The streams (i) and (ii) are each usually passed to the subsequent step, while the stream (iii) may be recycled for use as water for hydration.

Figure 3:
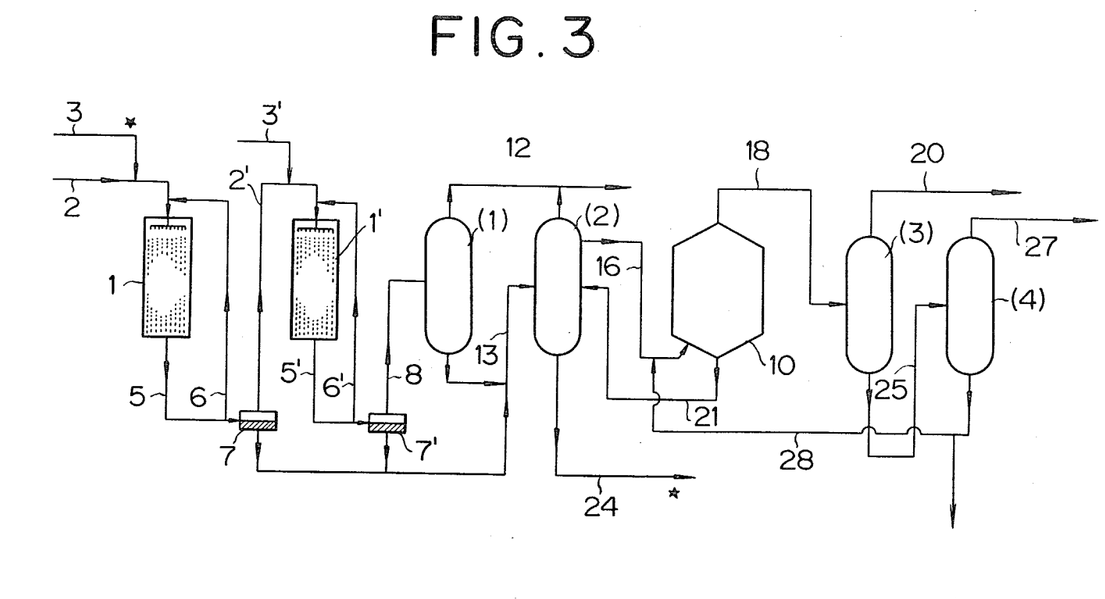

FIG. 1 illustrates that said separation into the three streams (fractions) is effected by the use of the two distillation towers. FIG. 3 also illustrates such separation, however, such separation may also be effected by the use of a single distillation tower. FIG. 1 also illustrates that the distillation-off or removal of the remaining unreacted hydrocarbons contained in the streams from the bottom of the distillation tower (1) and from the top of the distillation tower (2) is carried out in the single tower (2''); in addition, the streams from these towers (1) and (2) may be treated respectively in separate towers, such as the tower (2''), for the distillation-off of the remaining hydrocarbons. It is preferable, however, that such distillation-off is carried out in a single distillation tower. The effluent or stream from the distillation tower (2'') is supplied to the second reactor (dehydration reactor) 10. As stated before, the stream from the bottom of the distillation tower (1) is also supplied to the second reactor 10 in cases where the stream is not further subjected to distillation in another distillation tower.

These TBA-rich streams are continuously supplied to the second reactor 10 at a level thereof lower than the top of the reactor by at least two-thirds ($\frac{2}{3}$) of the height thereof.

The dehydration reactor used in this invention is a pressure-proof closed vessel provided at least with an inlet for a TBA feed, an outlet, provided at the upper portion of the vessel, for a gaseous mixture of the product and the unreacted TBA, and an outlet, provided at the lower portion thereof, for a liquid mixture of TBA and water.

As described later, as one of its features the dehydration reactor used herein may dispense with a device for the supply or removal of heat by the use of selected reaction conditions, however, it may have such a device as required.

The second reactor 10 is filled with the cation exchange resin catalyst and with a TBA-water liquid mixture in contact with the resin catalyst. It is preferable that this liquid mixture be present as a liquid phase throughout the greater part of the space, particularly in the space in which the catalyst is present, within the reactor. The liquid mixture is an aqueous solution containing TBA in an amount of about 2–70 wt.%, preferably 10–60 wt.%. The catalyst may be present in the form of a fixed bed or may also be present in the form of a suspension or fluidized bed in the liquid mixture of TBA and water.

It is preferable in the conduct of dehydration of TBA that a stirrer be provided in the reactor 10 or the circulation of the liquid mixture be effected by a pump thereby to keep the catalyst suspended or fluidized in the reactor 10. This is particularly convenient for continuously substituting the used and degraded catalyst by fresh catalyst.

The cation exchange resins which are used as a catalyst for dehydration in this invention, are a resin having acid groups and cation exchange capability and are typified by styrene-derived sulfonic acid type resins, phenol-derived sulfonic acid type resins and other strong acid type resins. Those having a hydrogen ion exchange capacity of at least 0.1 mM/g may be used. These typical exchange resins are the same as those used in said hydrating reaction. As one of those meeting this purpose, the used or waste catalyst withdrawn from the first reactor (hydration reactor) may be used as a catalyst for the second reactor 10 and the use of such waste catalysts is very effective in enhancing the economy of the process of this invention as a whole.

The second reactor 10 in which the catalyst and liquid mixture are housed, is maintained at a temperature of 90°–180° C., preferably 105°–140° C., and at a pressure of 1.5–15 Kg/cm$^2$G, preferably 3–10 Kg/cm$^2$G.

The TBA-rich stream is usually heated and supplied in a liquid or gaseous form to the second reactor 10 and it is preferable that the stream be supplied thereto at a pressure about 0.1–5 Kg/cm$^2$G higher than that in the reactor and at a temperature about 1°–50° C., for example, higher than that in the reactor. In some cases, however, the stream may be supplied at a temperature about 1°–30° C. lower than the temperature within the reactor to control the reaction temperature. In a case where the TBA-rich stream is supplied in the gaseous state, it is introduced into the liquid mixture in the reactor at a level lower than the upper level of the liquid layer by at least one-third ($\frac{1}{3}$), preferably a half to nine-tenths ($\frac{1}{2}$ to 9/10), of the height thereof. If the gaseous TBA be introduced into the liquid mixture at a level lower than is mentioned above, it will not react thoroughly with the result that the amount of the unreacted TBA withdrawn from the reactor at the top increases.

The TBA-rich stream is introduced is contacted with the liquid mixture of TBA and water already present at the predetermined temperature and pressure in the reactor to be absorbed and condensed in the mixture while being dehydrated on the surface of the catalyst also present in the reactor.

If the temperature used in the reactor is too low then the amount of isobutene produced will decrease, while if it is too high then the degradation of the catalyst will be accelerated with the disadvantage of use of a high-temperature heat source being incurred. In addition, if the pressure used is too low then the gaseous TBA introduced into the reactor will not fully be absorbed nor condensed with the result that an effective reaction is not effected. Further, if the pressure used is too high, then isobutene produced will have a high partial pressure in the reaction system thereby rendering it difficult to effect dehydration because of chemical equilibrium.

The introduction of the TBA-rich stream in the gaseous state will effectively economize or decrease the amount of heat externally supplied to the second reactor and also effectively control the temperature in the second reactor, thus achieving an effective dehydrating reaction of TBA.

Isobutene produced by the dehydrating reaction is withdrawn in the gaseous state from the reactor at the top to a line 18. This gaseous isobutene contains the unreacted TBA in the gaseous state and water in the steam form produced by the dehydration, and it may further contain a very minute amount of low polymers of isobutene (mainly dimer) produced as by-products.

This invention is practiced so that a ratio of conversion of TBA to isobutene achieved is 20–95%, preferably 30–90% and more preferably 40–80%. In cases where a satisfactorily high conversion ratio is not attained by the use of a single dehydration reactor, at least two (usually two or three) such reactors may be employed in series whereby not only such a conversion ratio is effectively increased but also a decrease in amount produced is inhibited at the time of replacing the used catalyst with fresh catalyst.

The gaseous mixture withdrawn from the dehydration reactor at the top comprises isobutene and TBA in an amount by weight of 1/10–2 parts, preferably 1/5–1 part, per part by weight of isobutene. The amount of TBA to remain unreacted in the gaseous mixture from the reactor may be controlled not to be too large by, for example, raising the reaction temperature and introducing the TBA-rich stream into the reactor through a supply inlet provided at a lower level.

The gaseous isobutene-containing stream withdrawn from the reactor at the top is treated to recover the isobutene from the stream. This recovery is attained by ordinary distillation. More particularly, the stream is introduced into a distillation tower (3) from which isobutene of high purity is obtained at the top connecting to a line 20 and a stream containing liquid TBA and a small amount of other impurities is obtained at the bottom connecting to a line 25. The liquid stream, without or after being heated, is supplied to the dehydration reactor. In this case, it is possible to inhibit isobutene dimer, secondary butanol and other impurities from accumulating in the system by withdrawing a part of the liquid stream therefrom. Further, preferably, the liquid stream is passed to a distillation tower (4) from which the greater part of isobutene dimer is withdrawn at the top connecting to a line 27 and a stream is withdrawn at the bottom and may then be recycled, without or after being heated, to the dehydration reactor connecting to a line 28. In this case, it is possible to inhibit secondary alcohol from accumulating in the system by discharging a part of the bottom stream therefrom.

On the other hand, a part of the liquid mixture of TBA and water is continuously withdrawn from the second reactor 10 at the bottom connecting to a line 21. This withdrawal will enable the level of the liquid phase or layer to be maintained constant and simultaneously enable the reaction to be carried out continuously and effectively.

The part of the liquid mixture stream so withdrawn contains the unreacted TBA, water and the greater part of the impurities originally present in the starting materials. When the reaction is being carried out continuously and stationarily, the mixture stream will have substantially the same composition as the liquid mixture of TBA and water in the reactor. An excess of water produced by the reaction and the unreacted TBA are removed by withdrawing said stream.

The stream passing through the line 21 is usually recycled for dehydration and, at this point, the mixture containing water and concentrated TBA is recovered from the distillation tower (2') at the top and then passed to the dehydration tower. On the other hand, a liquid stream containing the greater part of water is withdrawn from the tower at the bottom and it may be discharged from the system or recycled for use as water for hydration.

Figure 2:
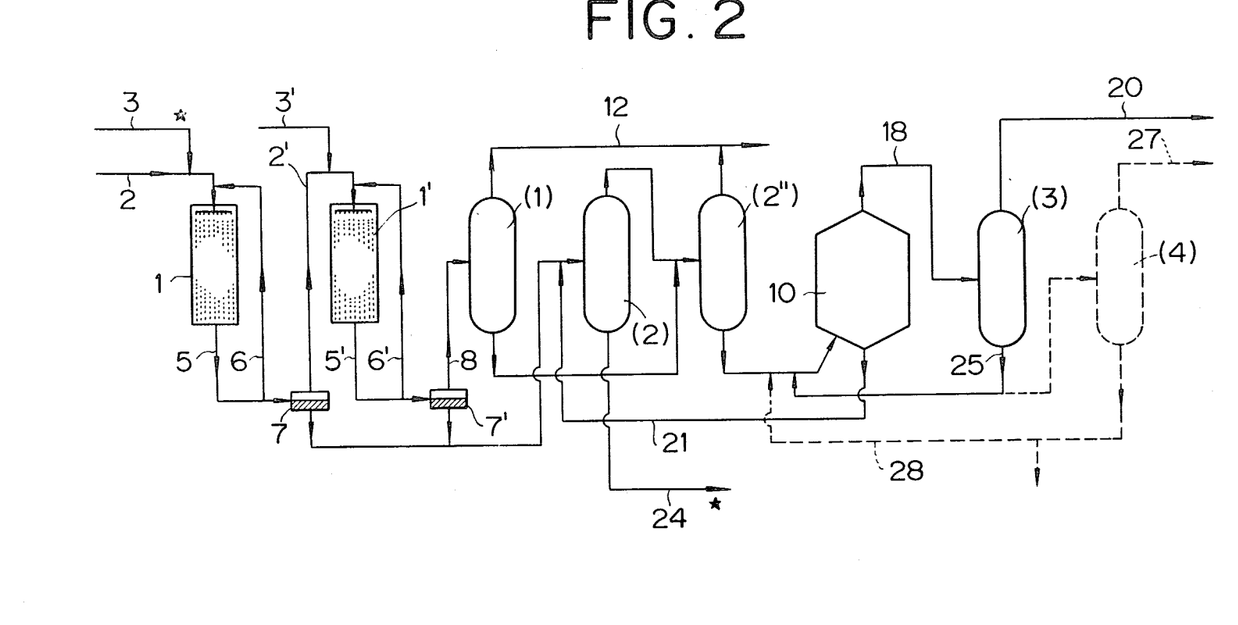

Further, as indicated in FIG. 2, it is one of the preferable procedures that the stream 21 and the stream of aqueous layer from the separation receptacle connecting to the first reactor are combined together, passed to the distillation tower (2) (in other words, these two streams are distilled in the same single distillation tower) to recover a stream containing TBA in the concentrated form from the tower (2) at the top and then passed to the stripping tower (2") to remove from the stream the unreacted hydrocarbons physically dissolved therein and then passed to the dehydration tower.

The procedure of FIG. 2 is in compliance with that of FIG. 1, however, it is characterized by the fact that the TBA-water mixture continuously withdrawn from the second reactor 10 and the aqueous layer from the receptacle 7 or 7' are simultaneously subjected to distillation in the distillation tower (2).

The procedure of FIG. 3 illustrates the most preferable one for practicing this invention and is explained hereinbelow.

The procedure of FIG. 3 is the same as that of FIG. 1 or 2 in the respects of the steps of hydration, separation of the hydration reaction mixture into hydrocarbon and aqueous layers in the receptacle and distillation of the thus separated hydrocarbon layer in the distillation tower (1).

In the procedure of FIG. 3, the TBA-rich stream from the distillation tower (1) is supplied to the distillation tower (2) to remove the remaining hydrocarbons therefrom. The stream of the aqueous layer from the receptacle 7 or 7' is also supplied to the distillation tower (2) and the TBA-water liquid mixture continuously withdrawn from the second reactor 10 is also supplied to the distillation tower (2).

The three effluents or streams withdrawn from the distillation tower (2) are as follows:

an unreacted hydrocarbon-containing stream withdrawn at the top (the stream being discharged outside the system, a water-rich stream withdrawn at the bottom (the aqueous stream being discharged outside the system or it being preferably recycled to the hydration reactor) and a TBA-rich stream withdrawn at the upper portion.

It is the most remarkable feature of the procedure of FIG. 3 to perform three distillation operations at the same time by the use of the distillation tower (2) having such functions as above. The three operations are as follows:

(a) The hydrocarbons remaining in the TBA-rich stream from the distillation tower (1) are further removed, (b) The aqueous stream from the separation receptacle is separated into three ones which are a stream (the lightest fraction) containing the remaining unreacted hydrocarbons, a TBA-rich stream and a water-rich stream and (c) The mixture of water and TBA in the concentrated state and the water-rich liquid stream are obtained from the aqueous stream from the receptacle.

In FIG. 3, the same reference numbers as in FIGS. 1 and 2 refer to the same apparatuses (such as reactors and towers) and lines as in FIGS. 1 and 2, respectively.

In this invention, as indicated by the above procedures, the TBA produced by the hydration is treated to regenerate the isobutene. In the procedures according to this invention, high temperatures and pressures are not particularly required, by-products are produced in satisfactorily less amounts, isobutene is obtained in a good yield and an external supply of heat for reactions is not or little necessary thereby rendering it possible to use large-sized reactors, this being industrially advantageous. Further, in the practice of this invention, the unreacted TBA is withdrawn at two points or sites, however, it may be easily recovered and recycled for re-use without incurring any inconveniences. Still further, in the practice of this invention, isobutene of high purity may still be obtained even from a starting material for TBA even if it contains impurities such as secondary butanol since it is in very few cases that the alcohol is decomposed to produce n-butene and the like.

The process of this invention further has the advantageous features that the by-products and the impurities physically dissolved in the C₄ hydrocarbon fraction as the starting material may be easily removed since they are all insoluble or sparingly soluble in water, isobutene may be easily obtained at high purity as the product, the amount of organic matter to be contained in the waste water may be limited to a small one by the use of ordinary means and the countermeasures against environmental pollution may be taken at a low cost.

In the process of this invention, the highest one of the temperatures used is 180° C. or lower and the pH used is kept at at least 3.5 whereby no problems are raised as to the corrosion of apparatuses used, the apparatuses may be constructed at a lower cost and the used catalyst from the first reactor for hydration may be used in the second reactor for dehydration as the catalyst, this increasing the economy of said process remarkably.

This invention will be better understood by the following non-limitative Examples.

EXAMPLE 1

In accordance with the procedure or process as indicated in FIG. 3, an experiment is made as follows.

A 14 cm-diameter and 60-liter cylindrical vessel for a hydration reactor is filled with 50 l of a strong acid type cation exchange resin previously wetted with a large amount of water, as the fixed bed catalyst to prepare the hydration reactor. The exchange resin used in this Example is one prepared by suspension polymerizing styrene and divinylbenzene in tertiary amyl alcohol as the solvent and has an exchange capacity of 3.6 meq/g, particle size of 0.4–0.6 mm, degree of crosslinking of 14%, surface area of 3.4 m²/g and porosity of 0.11 ml/ml. To the reactor so prepared are continuously supplied an isobutene-containing liquid C₄ hydrocarbon mixture and water by the use of a constant-volume pump. The C₄ mixture to be used is one prepared by extracting butadiene from a fraction obtained by the steam cracking of naphtha and has the following composition:

| isobutane | 5.0 wt.% |
|---|---|
| n-butane | 14.0 wt.% |
| trans . butene-2 | 7.2 wt.% |
| isobutene | 43.1 wt.% |
| butene-1 | 25.4 wt.% |
| cis . butene-2 | 5.2 wt.% |
| butadiene | 0.1 wt.% |

Prior to the commencement of hydration, water and the C₄ mixture are supplied as the starting materials, after being heated, to the hydration reactor through lines 3 and 2 at a flow rate of 12 l/hr and 25 l/hr, respectively, and the temperature in the reactor is raised to 85° C. while recycling the fluid at a rate of 100 l/hr through a line 6 from the outlet of the reactor, thereby to form a continuous phase of the C₄ mixture (as illustrated in FIG. 3). When the predetermined temperature is reached, the desired reaction starts and proceeds while supplying the starting materials respectively at the above flow rates and the pressure in the hydration reactor is maintained at a gauge pressure of 30 kg/cm² by continuously withdrawing therefrom the fluid in an amount substantially corresponding to the amount of the starting materials supplied. In this case, the linear velocity of the water is 2.9 m/hr, on the empty tower basis. The amount of the fluid withdrawn from the reactor at the outlet substantially corresponds to the total amount of the starting materials supplied through the lines 2 and 3, and the fluid so withdrawn is passed to an 8-l cylindrical separation receptacle where it is separated into a hydrocarbon layer and an aqueous layer. The hydrocarbon layer is passed through a line 8 to a distillation tower (1) having 20 theoretical stages, where it is distilled under a reflux ratio of 1. Thus, a raffinate C₄ mixture and a TBA-water mixture are recovered from the tower (1) at the top and bottom, respectively. The raffinate C₄ mixture is recovered at a flow rate of 16.8 l/hr in which 19.1 wt.% of isobutene is contained. A stream withdrawn from the tower (1) at the bottom, together with an aqueous stream from the separation receptacle, is supplied through a line 13 to a distillation tower (2) having 30 theoretical stages, where it is distilled under a reflux ratio of 2.5 thereby to discharge a small amount of C₄ hydrocarbons, isobutene dimer and the like from the tower at the top and recover a hot water containing about 200 ppm of SBA therefrom at the bottom. In addition, a TBA-water-SBA mixture having an approximate azeotropic composition is withdrawn at a flow rate of 7.02 Kg/hr (TBA: 83.7 wt.%, SBA: 3.8 wt.%, water: 12.5 wt.%) at the tenth stage from the top of the tower and passed through a line 16 to an evaporator where it is evaporated to form a mixed vapor at 135° C. which is then passed continuously through a scatterer to a dehydration reactor at the bottom. The dehydration reactor is a 10-l cylindrical one having a 16-cm diameter, provided with a stirrer and filled with 500 g of the same strong acid type cation exchange resin as filled in the hydration reactor and a 27.7 wt.% aqueous solution (containing 1.4 wt.% of SBA) of TBA, the resin and the solution totalling 8 liter in volume and being present in a solid-liquid mixed phase. When in the stationary state, the temperature and pressure in the dehydration reactor are 119° C. and 5 Kg/cm²G, respectively. The dehydration reactor is provided at the top with a line 18 through which produced isobutene, the unreacted TBA, steam, isobutene dimer produced as a byproduct, and the like are withdrawn in the gaseous state. The dehydration reactor is further provided with an automatic pressure control valve to maintain the pressure within the reactor at 5 Kg/cm²G. A line 21 through which a liquid mixture of TBA, water and SBA is withdrawn (through a screen to filter out the catalyst) from the dehydration reactor at the bottom, is provided with an automatic adjusting valve thereby to maintain the solidliquid mixture at such a level that the volume of the mixture is 8 liter in the reactor. A gaseous mixture obtained from the dehydration reactor at the top is passed to a distillation tower (3) having 30 theoretical stages where it is distilled under a reflux ratio of 1.5 to recover 4.42 Kg/hr of isobutene therefrom. The isobutene so recovered contains as the impurities 110 ppm of butanes, 130 ppm of butene-1, 250 ppm of butene-2, 15 ppm of isobutene dimer and a small amount of water, and the purity of isobutene is 99.95 wt.% based on the isobutene except for the water. A fraction (or stream) withdrawn from the distillation tower (3) at the bottom is passed through a line 25 to a distillation tower (4) having 10 theoretical stages where it is distilled under a reflux ratio of 1 thereby to discharge isobutene dimer at a flow rate of 0.019 kg/hr from the tower at the top and withdraw a fraction (an 84.3 wt.% aqueous solution of TBA) therefrom at the bottom. The fraction so withdrawn is partly bled to remove SBA therefrom, passed through a line 28 to an evaporator for evaporation and then recycled, together with the stream flowing through the line 16, to the dehydration reactor.

A liquid stream withdrawn through the line 21 from the dehydration reactor contains 27.7 wt.% of TBA. This liquid stream is passed, together with the stream flowing through the line 13, to the distillation tower (2) for distilling them thereby to recover an 87.3 wt.% aqueous solution of TBA which is, after being heated to form a vapor, recycled through the line 16 to the dehydration reactor. Hot water is recovered from the distillation tower (2) at the bottom, and the greater part thereof is then recycled as the water supply source to the hydration reactor.

The above procedure is continuously repeated and, as a result, the ratio of recovery of isobutene from the $C_4$ mixture is 68.4% and the selectivity (purity) of isobutene is 99.5%. Further, the cation exchange resin used as the catalyst is not appreciated to have been degraded even after its use for 2,000 hours.

EXAMPLE 2

In accordance with the procedure of FIG. 3, an experiment is made as follows.

The same three vessels for hydration reactor as used in Example 1 are each filled with 50 l of a strong acid type cation exchange resin as the fixed bed to prepare first to third hydration reactors. The strong acid type cation exchange resin used in this Example is one prepared by suspension polymerizing styrene and divinylbenzene in tertiary amyl alcohol as the solvent, and it has an exchange capacity of 3.2 meq/g, particle size of 0.2–0.8 mm, crosslinking degree of 10%, surface area of 0.72 $m^2/g$ and porosity of 0.06 ml/ml. Prior to starting hydration, the first hydration reactor is cooled to 5° C. and filled with a liquid isobutene-containing $C_4$ hydrocarbon mixture to form a continuous phase of the $C_4$ mixture. Then, the $C_4$ mixture and water are supplied through lines 2 and 3 to the first hydration reactor in gradually increasing amounts and finally at flow rates of 25 l/hr and 12 l/hr, respectively. At this point, the first hydration reactor is maintained at a temperature of 90° C. and a pressure of 20 $Kg/cm^2G$. The $C_4$ mixture used in this Example is the same as used in Example 1. While recycling 100 l/hr of the fluid through a line 6 to the first hydration reactor, the fluid is introduced into a first cylindrical separation receptacle in an amount substantially corresponding to the total amount of fresh starting materials supplied through the lines 2 and 3. In the receptacle the fluid so introduced is separated into a hydrocarbon layer and an aqueous layer. At this point, the linear velocity of the water in the reactor is 2.9 m/hr, based on the empty reactor. The hydrocarbon layer withdrawn through a line 2' is subjected to flash distillation to remove TBA therefrom. The TBA is passed to a distillation tower (2) while the remaining $C_4$ mixture is cooled to be liquefied and passed through the line 2' to the second hydration reactor to which 12 l/hr of water is simultaneously supplied through a line 3'.

The second hydration reactor already contains a liquid hydrocarbon layer in the continuous phase formed in the same manner as in the first hydration reactor and is maintained at a temperature of 90° C. and a pressure of 20 $Kg/cm^2G$. The hydrating reaction in the second hydration reactor proceeds in the same manner as in the first hydration reactor, and the fluid withdrawn from the second hydration reactor is passed to a second separation receptacle where it is separated into an aqueous layer and a hydrocarbon layer which is then passed through the line 2' to the third hydration reactor (not shown). At this point, 12 l/hr of water is supplied through the line 3' (not shown) to the third hydration reactor as in the first and second hydration reactors. The third hydration reactor already has a liquefied hydrocarbon layer in the continuous phase formed therein, and the reaction conditions for the third reactor such as the temperature, pressure and amount of the fluid recycled are identical with those for the first or second hydration reactor.

The hydrocarbon layer from a third separation receptacle is passed through a line 8 to a distillation tower (1) having 20 theoretical stages to distil it under the reflux ratio of 1. Thus, a raffinate $C_4$ mixture is recovered from the tower (1) at the top while the TBA and water are recovered therefrom at the bottom. The raffinate $C_4$ mixture is recovered at a flow rate of 14.4 l/hr and contains 3.5 wt.%. The stream from the bottom of the tower (1), together with the aqueous layers from the three separation receptacles and the hydrocarbon layer withdrawn from the first separation receptacle and then subjected to flash distillation, is passed through a line 13 to the distillation tower (2) where the resulting mixture is distilled under the reflux ratio of 2.0 thereby to discharge a small amount of the $C_4$ mixture, isobutene dimer and the like from the tower (2) at the top and recover a hot water containing about 510 ppm of SBA therefrom at the bottom. In addition, a TBA-water-SBA mixture which has an approximate azeotropic composition, is withdrawn at a flow rate of 9.58 Kg/hr (TBA 84.9 wt.%, SBA 3.5 wt.%, water 11.6 wt.%) from the tower (2) at a level corresponding to the tenth stage from the top and passed through a line 16 to an evaporator to form a mixed vapor at 133° C. which is continuously supplied through a scatterer to a dehydration reactor at the bottom. The dehydration reactor is of the same structure as used in Example 1 and is filled with a suspension of 760 g of the strong acid type cation exchange resin previously used for 8,000 hr in the hydration reactor, in a 30.8 wt.% aqueous solution (containing 1.1 wt.% of SBA), and the amount of the liquid withdrawn is controlled so that the cation exchange resin-containing liquid layer present in the reactor is 8 liters in volume. When in the stationary state, the temperature and pressure within the dehydration reactor are 115° C. and 6 $Kg/cm^2G$, respectively. The reactor is provided with a line 18 through which produced isobutene, the unreacted TBA, steam, isobutene dimer and the like are withdrawn in the gaseous state and it is further provided with an automatic pressure control valve thereby to maintain the pressure within the reactor at a pressure of 6 $Kg/cm^2G$.

In addition, a TBA-water-SBA liquid mixture is withdrawn, after being filtered with a screen to remove the catalyst, from the dehydration reactor at the bottom and then passed through a line 21 provided with an automatic valve thereby to keep the liquid level at a level corresponding to 8 liters of the liquid. The gaseous mixture withdrawn from the dehydration reactor at the top is passed to a distillation tower (3) where it is distilled under the reflux ratio of 1.5 to recover 6.11 Kg/hr of isobutene. The isobutene so recovered contains as the impurities 220 ppm of butanes, 160 ppm of butene-1, 210 ppm of butene-2, 65 ppm of isobutene dimer and a small amount of water, and it has a purity of 99.93 wt.% based on the isobutene except for the water. The fraction or stream from the distillation tower (3) at the bottom is passed through a line 25 to a distillation tower (4) having 10 theoretical stages where it is distilled under the reflux ratio of 1 thereby to discharge 0.031 Kg/hr of isobutene dimer at the top and withdraw a fraction (an 81.1 wt.% aqueous solution of TBA) which is partly bled to remove SBA and recycled through a line 28 to the dehydration reactor.

A liquid stream withdrawn through the line 21 from the dehydration reactor contains 30.8 wt.% of TBA, is passed, together with the stream flowing through the line 13, to the distillation tower (2) where the resulting mixture is distilled to recover an aqueous solution of TBA which is then recycled through the line 16 to the dehydration reactor. Hot water is recovered from the distillation tower (2) at the bottom, and the greater part thereof is recycled as a water supply source to the hydration reactor.

The above procedure is continuously repeated and, as a result, the ratio of recovery of isobutene from the $C_4$ mixture is 94.5% and the selectivity (purity) of isobutene obtained is 99.5%.

EXAMPLE 3

In accordance with the flow sheet of FIG. 1, an experiment is made as follows.

Using the same hydration reactors (reactors 1 and 1'), catalyst and $C_4$ mixture as used in Example 1, hydration is effected. In the reactors a liquid hydrocarbon layer in the continuous phase is already formed in the same manner as Example 1. A $C_4$ mixture is supplied at a flow rate of 25 l/hr through a line 2 to a series of the hydration reactors maintained at 90° C. and 20 Kg/cm²G to effect hydration on the $C_4$ mixture in the same manner as in Example 1. TBA separated by flash distillation between the reactors 1 and 1' is combined with a hydrocarbon layer from a separation receptacle 7' to form a mixture which is then supplied to a distillation tower (1).

The distillation tower (1) has 20 theoretical stages, in which distillation is effected under the reflux ratio of 1 thereby to recover a raffinate $C_4$ mixture through a line 12 at the top and recover water and TBA at the bottom. The raffinate $C_4$ mixture is recovered at a flow rate of 16.4 l/hr and it contains 13.2 wt.% of isobutene. On the other hand, aqueous layers from separation receptacles 7 and 7' are supplied to a distillation tower (2) having 30 theoretical stages where they are distilled under the reflux ratio of 2.5 thereby to recover TBA of 87.5 wt.% at the top and recover hot water containing 3,300 ppm of SBA. TBA-containing streams from the bottom of the distillation tower (1) and the top of the distillation tower (2) are combined together and supplied to a stripping tower (2''). From the stripping tower (2'') which is one having several ten theoretical stages, the unreacted hydrocarbon in the gaseous state is recovered at a flow rate of 38 l/hr at the top and a stream withdrawn at the bottom is heated to 135° C. and then continuously supplied through a scatterer to a second reactor 10 (dehydration reactor) at the bottom.

The dehydration reactor 10 is a 10-l cylindrical one having a 16-cm diameter and being provided with a stirrer, and it contains 2000 g of the same strong acid type cation exchange resin as contained in the hydration reactors and a 28.0 wt.% aqueous solution (containing 1.4 wt.% of SBA) of TBA, the exchange resin and the aqueous solution being present in the solid-liquid mixed phase having a volume of 8 liters. When in the stationary state, the temperature and pressure of the dehydration reactor are 110° C. and 4 Kg/cm²G, respectively.

The dehydration reactor is connected at the top to a line 18 through which isobutene produced, the unreacted TBA, steam, isobutene dimer as a by-product, and the like are withdrawn in the gaseous state. The reactor is also provided at the top with an automatic pressure control valve to keep the pressure in the reactor at a pressure of 4 Kg/cm²G.

A line 21 through which a TBA-water-SBA liquid mixture is withdrawn, after being filtered with a screen to remove the catalyst, from the dehydration reactor at the bottom, is provided with an automatic control valve to maintain the solid-liquid mixture at such a level that it has a volume of 8 liters in the reactor. A gaseous mixture withdrawn from the dehydration reactor at the top is passed to a distillation tower (3) having 30 theoretical stages where it is distilled under the reflux ratio of 1.5 thereby to recover 4.98 Kg/hr of isobutene. This isobutene contains as the impurities 90 ppm of butanes, 120 ppm of butene-1, 300 ppm of butene-2, 15 ppm of isobutene dimer and a small amount of water, and it has a purity of 99.95 wt.% based on the empty tower except for the water. A fraction or stream from the distillation tower (3) at the bottom is passed through a line 25 to a distillation tower (4) having 10 theoretical stages where it is distilled under the reflux ratio of 1 thereby to discharge isobutene dimer at 0.020 Kg/hr at the top and recycle a fraction, after being partly bled to remove SBA, to the dehydration reactor.

A liquid stream withdrawn through the line 21 from the dehydration reactor contains 28.0 wt.% of TBA and it is passed to a distillation tower (2') where it is distilled thereby to recover an 88.0 wt.% aqueous solution of TBA which is, after being heated, recycled to the dehydration reactor. Hot water is recovered from the distillation towers (2) and (2') at the bottom, and the greater part thereof is recycled as a water supply source to the hydration reactor.

The above procedure is continuously repeated and, as a result, the ratio of recovery of isobutene from the $C_4$ mixture is 77.0%. The cation exchange resin is not appreciated to have been degraded even after its use for 2,000 hours.

EXAMPLE 4

In accordance with the flow sheet of FIG. 2, an experiment is made as follows.

Hydration is effected in the same manner as in Example 1.

TBA separated by flash distillation between first reactors (hydration reactors) 1 and 1' and a hydrocarbon layer from a separation receptacle 7' are combined together and passed to a distillation tower (1) having 20 theoretical stages. A mixture of the TBA and hydrocarbon layer is distilled under the reflux ratio of 1 in the tower (1) thereby to recover a raffinate $C_4$ mixture through a line 12 from the tower at the top and recover water and TBA therefrom at the bottom. The raffinate $C_4$ mixture is recovered at a flow rate of 16.4 l/hr and contains 13.2 wt.% of isobutene. On the other hand, an aqueous stream from separation receptacles 7 and 7' and a liquid stream from a second reactor (dehydration reactor) at the bottom are combined together and passed to a distillation tower (2) having 30 theoretical stages where the combined streams are distilled under the reflux ratio of 2 thereby to recover a TBA-rich stream containing 87 wt.% of TBA at the top and recover hot water containing 2,200 ppm of SBA at the bottom. TBA-containing streams withdrawn from the distillation tower (1) at the bottom and from the distillation tower (2) at the top are passed together to a stripping tower (2"), which is a distillation tower, having 10 theoretical stages where they are subjected to stripping thereby to recover 38 l/hr of the unreacted hydrocarbon in the gaseous state at the top and recover a TBA-rich stream at the bottom, the TBA-rich stream being heated to 135° C. and continuously supplied through a scatterer to a second reactor 10 (dehydration reactor) at the lower portion.

The dehydration reactor is a 10-l cylindrical vessel having a 16-cm diameter and provided with a stirrer. The dehydration reactor contains 2,000 g of the same strong acid type cation exchange resin as contained in the hydration reactors and a 29.2 wt.% aqueous solution (containing 1.4 wt.% of SBA) of TBA, the exchange resin and the aqueous solution are present to have a volume of 8 liters in total in the solid-liquid mixed phase in the reactor. When in the stationary state, the temperature and pressure within the dehydration reactor are 120° C. and 6 $Kg/cm^2G$, respectively. The reactor is connected at the top to a line 18 through which isobutene produced, the unreacted TBA, steam, isobutene dimer produced as a by-product, and the like are withdrawn in the gaseous state. The reactor is further provided at the top with an automatic pressure control valve thereby to maintain the pressure in the reactor at 6 $Kg/cm^2G$.

Further, a line 21 through which a TBA-water-SBA liquid mixture is withdrawn, after being separated from the catalyst by a screen, from the dehydration reactor at the bottom, is fitted with an automatic control valve thereby to maintain the volume of the solid-liquid mixture at a level of 8 liters in the reactor. A gaseous mixture withdrawn from the dehydration reactor at the top is passed to a distillation tower (3) where it is distilled under the reflux ratio of 1.5 thereby to recover 5.11 Kg/hr of isobutene. The isobutene so recovered contains as the impurities 100 ppm of butanes, 120 ppm of butene-1, 400 ppm of butene-2, 120 ppm of isobutene dimer and a small amount of water. The purity of isobutene obtained is 99.92 wt.% as dry matter (when disregarding the water content). A fraction (an 82.4 wt.% aqueous solution of TBA) withdrawn from the distillation tower (3) at the bottom is partly bled to remove the SBA and isobutene dimer therefrom and then recycled through a line 28 to the dehydration reactor.

A liquid fraction withdrawn through the line 21 from the dehydration reactor contains 29.2 wt.% of TBA and it is passed to the distillation tower (2) for distillation, heated and then recycled to the dehydration reactor. The greater part of hot water recovered from the distillation tower (2) at the bottom is recycled as a water supply source to the hydration reactor.

The above procedure is continuously repeated and, as a result, the ratio of recovery of isobutene from the $C_4$ mixture is 79.0%.

What is claimed is:

1. A process for the continuous separation and recovery of isobutene comprising the steps of:
   (1) contacting an isobutene-containing hydrocarbon mixture with water in the presence of a cation exchange resin as the catalyst to obtain a reaction mixture containing tertiary butanol,
   (2) separating the thus obtained tertiary butanol-containing mixture into a hydrocarbon layer and an aqueous layer,
   (3) distilling the hydrocarbon layer to recover the unreacted hydrocarbons as the top and obtain a tertiary butanol-rich stream as the bottoms,
   (4) distilling the aqueous layer from the step (2) to obtain the following three streams:
      (i) a stream, which is a lighter fraction, containing the unreacted hydrocarbons which remained in said aqueous layer,
      (ii) a tertiary butanol-rich stream, and
      (iii) a water-rich stream,
   (5) introducing the tertiary butanol-rich stream from the step (3) and the tertiary butanol-rich stream (ii) from the step (4) continuously into a dehydration reactor containing a cation exchange resin catalyst and a liquid mixture of 20–70 wt.% of tertiary butanol with water at a temperature of 90°–180° C. and a pressure of 1.5–15 $Kg/cm^2G$, to effect the dehydration of the tertiary butanol,
   (6) withdrawing a mixture of gaseous isobutene, gaseous unreacted tertiary butanol and steam continuously from the top of said dehydration reactor,
   (7) introducing the thus withdrawn gaseous mixture from step (6) into a distillation tower to recover isobutene as the product therefrom at the top while recycling at least a part of the remaining fraction to said dehydration reactor in step (5),
   (8) withdrawing continuously from said dehydration reactor a part of the liquid mixture of the unreacted tertiary butanol and water contained therein and
   (9) subjecting the thus withdrawn liquid mixture of step (8) to distillation in a distillation tower to withdraw a liquid stream from the bottom of said tower containing the major portion of the water in said mixture and to separate from the top of said tower a mixture containing a major portion of tertiary butanol and a minor portion of water, and said mixture of butanol and water being recycled to said dehydration reactor.

2. A process according to claim 1, wherein the tertiary butanol-rich stream obtained in the step of (3) is further distilled to remove the remaining hydrocarbons therefrom just before being introduced into said dehydration reactor.

3. A process according to claim 1 or 2, wherein the distillation to obtain the three streams in the step of (4) is effected using a single distillation tower.

4. A process according to claim 1 or 2, wherein the distillation to obtain the three streams in the step of (4) is effected using two distillation towers arranged in series in such a manner that one of the distillation towers is used to obtain the water-rich stream (iii) and the other is used to obtain the unreacted hydrocarbon-containing stream (i) and the tertiary butanol-containing stream (ii).

5. A process according to claim 3, wherein the tertiary butanol-rich stream from said step (3) is further distilled just before being introduced into the dehydration reactor to remove the remaining hydrocarbons therefrom, the further distillation being effected in the same single distillation tower that is used in claim 3.

6. A process according to claim 4, wherein the tertiary butanol-rich stream from said step (3) is further distilled to remove the remaining hydrocarbons therefrom just before being introduced into the dehydration reactor, the further distillation is effected in the same distillation tower that is used to obtain the unreacted hydrocarbon-containing stream in claim 4.

7. A process according to claim 3, wherein the distillation of the step (9) is effected in the same single distillation tower that is used in claim 3.

8. A process according to claim 4, wherein the distillation of the step (9) is effected in the same distillation tower that is used to obtain the water-rich stream (iii) in claim 4.

9. A process according to claim 7, wherein the tertiary butanol-rich stream from said step (3) is further distilled just before being introduced into the dehydration reactor to remove the remaining hydrocarbons therefrom, the further distillation being effected in the same single distillation tower that is used in claim 7.

10. A process according to claim 4, wherein the tertiary butanol-rich stream obtained from the step (3) is further distilled to remove the remaining hydrocarbons therefrom just before being introduced into the dehydration reactor, the further distillation being effected in the same other distillation tower that is used to obtain the unreacted hydrocarbon-containing stream (i) in claim 4 and the distillation of said step (9) being effected in the same distillation tower that is used to obtain the water-rich stream (iii) in claim 4.

11. A process according to claim 10, wherein the remaining fraction from said step (7) is, just before being introduced into the dehydration reactor, distilled in a distillation tower to discharge the greater part of isobutene dimer therefrom at the top while recycling a stream withdrawn from the tower at the bottom to the dehydration reactor.

12. A process according to claim 1, wherein the reaction mixture containing tertiary butanol is obtained by supplying an isobutene-containing hydrocarbon mixture and water continuously to a hydration reactor containing a strong acid type cation exchange resin catalyst particles as the fixed bed the gaps among the catalyst particles are filled with said isobutene-containing hydrocarbon mixture in the continuous phase, the water descending along the surfaces of the catalyst particles at a linear velocity of at least 1.0 m/hr, and contacting at 50°–150° C. the isobutene-containing hydrocarbon mixture with the water continuously to effect a hydrating reaction therebetween.

13. A process according to claim 1, wherein the two tertiary butanol-rich streams in said step (5) are converted to a gas having a higher pressure than the inside of the dehydration reactor just before being introduced thereinto.

14. A process according to claim 1, wherein the tertiary butanol-water mixture in the dehydration reactor contains 10–60 wt.% of tertiary butanol.

* * * * *

UNITED STATES PATENT AND TRADEMARK OFFICE
CERTIFICATE OF CORRECTION

PATENT NO. : 4,208,540
DATED : June 17, 1980
INVENTOR(S) : Masao IMAIZUMI et al.

It is certified that error appears in the above–identified patent and that said Letters Patent are hereby corrected as shown below:

Column 2, line 19, change "20-70" to -- 2-70 --.

Claim 1, column 18, line 15, change "20-70" to -- 2-70 --.

Signed and Sealed this

Tenth Day of November 1981

[SEAL]

*Attest:*

*Attesting Officer*

GERALD J. MOSSINGHOFF

*Commissioner of Patents and Trademarks*